(12) United States Patent
Alkhatib

(10) Patent No.: US 11,974,915 B2
(45) Date of Patent: *May 7, 2024

(54) PROSTHETIC AORTIC HEART VALVES

(71) Applicant: St. Jude Medical, LLC, Abbott Park, IL (US)

(72) Inventor: Yousef F. Alkhatib, Edina, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 322 days.

This patent is subject to a terminal disclaimer.

(21) Appl. No.: 17/463,636

(22) Filed: Sep. 1, 2021

(65) Prior Publication Data

US 2021/0393400 A1 Dec. 23, 2021

Related U.S. Application Data

(60) Division of application No. 16/655,963, filed on Oct. 17, 2019, now Pat. No. 11,141,267, which is a
(Continued)

(51) Int. Cl.
*A61F 2/24* (2006.01)
(52) U.S. Cl.
CPC .......... *A61F 2/2418* (2013.01); *A61F 2/2409* (2013.01); *A61F 2/2445* (2013.01);
(Continued)
(58) Field of Classification Search
None
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

"Closed heart surgery: Back to the future", Samuel V. Lichtenstein, The Journal of Thoracic and Cardiovascular Surgery, vol. 131, No. 5, pp. 941-943.
(Continued)

*Primary Examiner* — Leslie A Lopez
(74) *Attorney, Agent, or Firm* — SLEMAN & LUND LLP

(57) ABSTRACT

A prosthetic aortic valve includes an annular, annulus inflow portion that is designed to reside in or near the patient's native aortic valve annulus, and an annular, aortic outflow portion that is designed to reside in the patient's aorta downstream from at least a portion of the valsalva sinus. The annulus inflow portion and the aortic outflow portion are connected to one another by a plurality of connecting struts that are confined to regions near the commissures of the patient's native aortic valve. The connecting struts are designed to bulge out into the valsalva sinus to help anchor the prosthetic valve in place. The valve is circumferentially collapsible to a relatively small diameter for less-invasive delivery into the patient. The valve circumferentially expands to a larger operational diameter when deployed at the implant site.

17 Claims, 12 Drawing Sheets

Related U.S. Application Data continuation of application No. 15/923,449, filed on Mar. 16, 2018, now Pat. No. 10,485,662, which is a continuation of application No. 15/206,427, filed on Jul. 11, 2016, now Pat. No. 9,949,826, which is a continuation of application No. 14/261,628, filed on Apr. 25, 2014, now Pat. No. 9,421,097, which is a continuation of application No. 12/733,344, filed as application No. PCT/US2008/009950 on Aug. 21, 2008, now Pat. No. 8,728,154.

(60) Provisional application No. 60/966,113, filed on Aug. 24, 2007.

(52) U.S. Cl.
CPC .............. *A61F 2220/0016* (2013.01); *A61F 2220/0075* (2013.01); *A61F 2230/0017* (2013.01); *A61F 2230/0054* (2013.01); *A61F 2230/0076* (2013.01)

(56) References Cited

U.S. PATENT DOCUMENTS

| | | | |
|---|---|---|---|
| RE30,912 E | 4/1982 | Hancock | |
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |
| 5,415,664 A | 5/1995 | Pinchuk | |
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,458,153 B1 | 10/2002 | Bailey et al. | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,857,845 B2 | 12/2010 | Stacchino et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 8,840,661 B2 | 9/2014 | Manasse | |
| 8,840,663 B2 | 9/2014 | Salahieh et al. | |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2003/0209835 A1 | 11/2003 | Chun et al. | |
| 2004/0049262 A1 | 3/2004 | Obermiller et al. | |
| 2004/0093060 A1* | 5/2004 | Seguin | A61F 2/2418 623/1.11 |
| 2004/0093075 A1 | 5/2004 | Kuehne | |
| 2004/0186563 A1* | 9/2004 | Lobbi | A61F 2/2436 623/2.11 |
| 2004/0210304 A1 | 10/2004 | Seguin et al. | |
| 2005/0096726 A1 | 5/2005 | Sequin et al. | |
| 2005/0096731 A1 | 5/2005 | Looi et al. | |
| 2005/0096734 A1 | 5/2005 | Majercak et al. | |
| 2005/0137695 A1 | 6/2005 | Salahieh et al. | |
| 2005/0137697 A1 | 6/2005 | Salahieh et al. | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1* | 8/2006 | Stacchino | A61F 2/848 623/2.18 |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |

(56) References Cited

U.S. PATENT DOCUMENTS

| | | |
|---|---|---|
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0171447 A1 | 7/2009 | Von Segesser et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2012/0303116 A1 | 11/2012 | Gorman, III et al. |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1690515 A1 | 8/2006 |
| EP | 1926455 A2 | 6/2008 |
| FR | 2850008 A1 | 7/2004 |
| FR | 2847800 B1 | 10/2005 |
| JP | 2007509701 A | 4/2007 |
| NO | 2008150529 A1 | 12/2008 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 200128459 A1 | 4/2001 |
| WO | 200149213 A2 | 7/2001 |
| WO | 200156500 A2 | 8/2001 |
| WO | 2001054625 A1 | 8/2001 |
| WO | 200176510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 2007071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

"Direct-Access Valve Replacement", Christoph H. Huber, et al., Journal of the American College of Cardiology, vol. 46, No. 2, (Jul. 19, 2005).

"Minimally invasive cardiac surgery", M. J. Mack, Surgical Endoscopy, 2006, 20:S488-S492, DOI: 10.1007/s00464-006-0110-8 (presented Apr. 24, 2006).

"Percutaneous Aortic Valve Implantation Retrograde From the Femoral Artery", John G. Webb et al., Circulation, 2006; 113:842-850 (Feb. 6, 2006).

"Transapical aortic valve implantation: an animal feasibility study"; Todd M. Dewey et al., The annals of thoracic surgery 2006; 82: 110-6 (Feb. 13, 2006).

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical Transcatheter Aortic Valve Implantation in Humans", Samuel V. Lichtenstein et al., Circulation. 2006; 114: 591-596 (Jul. 31, 2006).

Braido, et al., U.S. Appl. No. 29/375,243, filed Sep. 20, 2010, titled "Surgical Stent Assembly".

Catheter-implanted prosthetic heart valves, Knudsen, L.L., et al., The International Journal of Artificial Organs, vol. 16, No. 5 1993, pp. 253-262.

EP 12165625.0 Extended European Search Report for Application No. EP 12165625.0 dated Apr. 3, 2014.

International Search Report for Application No. PCT/US2008/009950 dated Dec. 2, 2009.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

Partial European Search Report for Application No. 12165625.0 dated Dec. 6, 2013.

Ruiz, Carlos, Overview of PRE-CE Mark Transcatheter Aortic Valve Technologies, Euro PCR (powerpoint) dated May 25, 2010?

Textbook "Transcatheter Valve Repair", 2006, pp. 165-186.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

\* cited by examiner

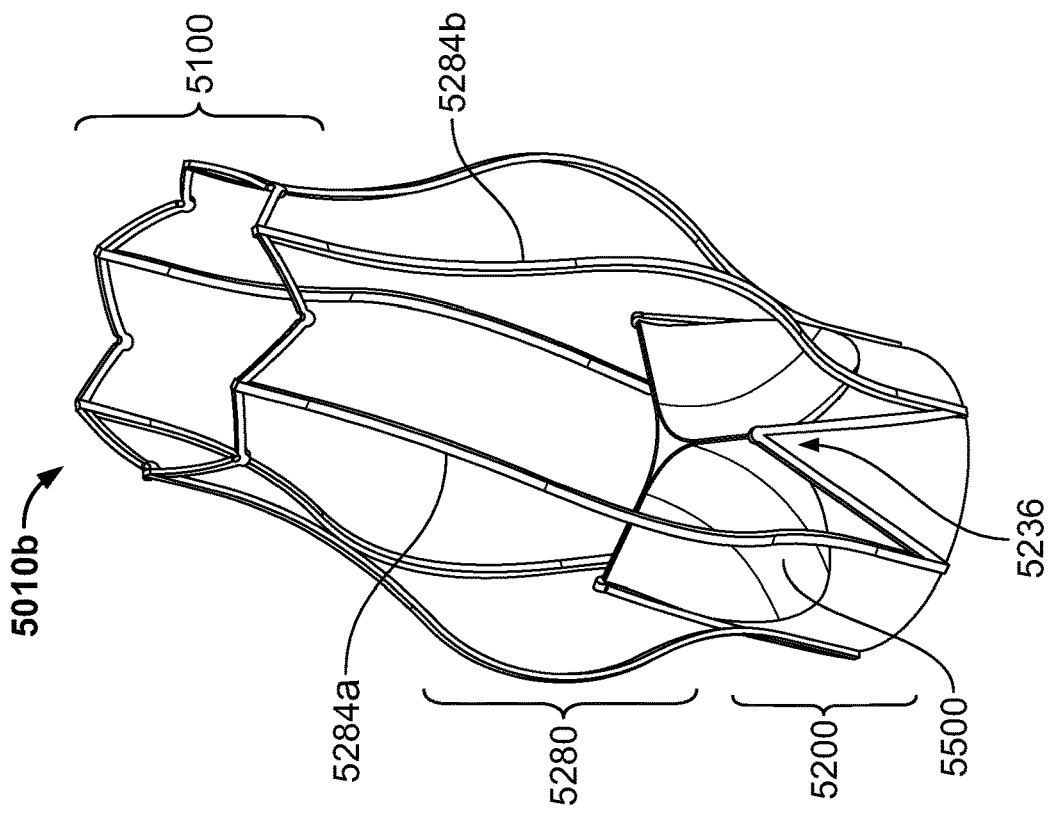
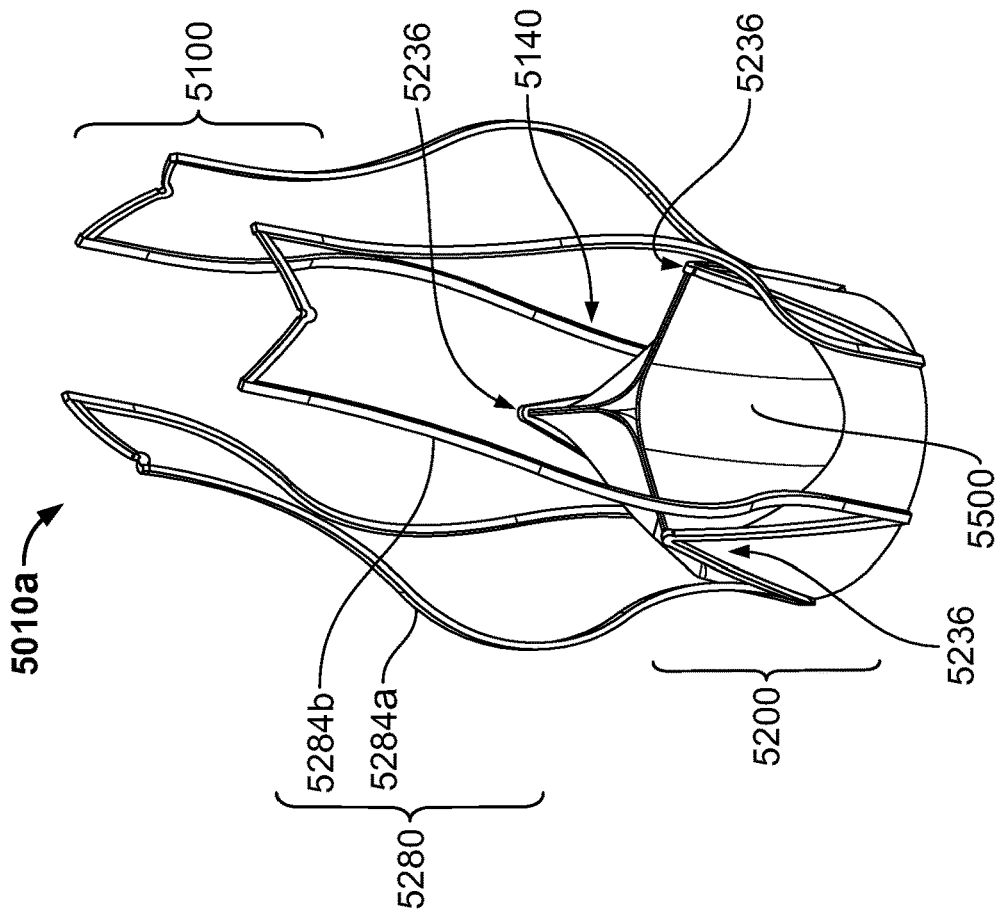

PROSTHETIC AORTIC HEART VALVES

The present application is a division of U.S. patent application Ser. No. 16/655,963, filed on Oct. 17, 2019, which is a continuation of U.S. patent application Ser. No. 15/923,449, filed on Mar. 16, 2018, now U.S. Pat. No. 10,485,662, which is a continuation of U.S. patent application Ser. No. 15/206,427, filed on Jul. 11, 2016, now U.S. Pat. No. 9,949,826, which is a continuation of U.S. patent application Ser. No. 14/261,628, filed on Apr. 25, 2014, now U.S. Pat. No. 9,421,097, which is a continuation of U.S. patent application Ser. No. 12/733,344, filed on Feb. 24, 2010, now U.S. Pat. No. 8,728,154, which application is a national phase entry under 35 U.S.C. § 371 of International Application No. PCT/US08/09950, filed Aug. 21, 2008, which claims priority from U.S. Provisional Patent Application No. 60/966,113, filed Aug. 24, 2007, the disclosures of all of which are incorporated herein by reference.

BACKGROUND OF THE INVENTION

PCT patent application No. PCT/US08/07015, filed Jun. 4, 2008, shows prosthetic heart valves that are annularly collapsible for delivery into a patient, and then re-expandable at the implant site in the patient. (The above document will be referred to hereinafter as the above-mentioned reference, and it is hereby incorporated by reference herein in its entirety.) The prosthetic heart valves shown and described in the above-mentioned reference typically include an annular supporting structure or stent frame (e.g., of a highly elastic metal such as nitinol). This stent frame or stent typically includes an annulus inflow portion and an aortic outflow portion that is generally coaxial with the annulus inflow portion and spaced downstream (in terms of blood flow through the implanted valve) from the annulus inflow portion. The annulus inflow and aortic outflow portions are preferably connected to one another substantially solely by connecting struts that extend between the annulus inflow and aortic outflow portions adjacent to the commissure regions (also known as commissure posts having commissure tips) of the valve. By confining these connecting struts between the annulus inflow and aortic outflow portions to close proximity to the commissure tip regions, the circumferential space between annularly adjacent commissure tips is left relatively open, which (in the case of aortic valve use) helps the prosthesis avoid occluding the ostia of the coronary arteries.

Valves of this general type are intended for delivery into a patient at an implant site to which the surgeon may not have direct open access, e.g., for suturing the implanted valve in place. Good self-anchoring of the valve at the implant site is therefore important, and there may be self-anchoring improvements that can be made relative to embodiments that are shown in the above-mentioned reference.

SUMMARY OF THE INVENTION

A prosthetic aortic valve in accordance with the invention typically includes an annular stent frame and a plurality of valve leaflets supported by a portion of the stent. The stent typically includes an annulus inflow portion configured for disposition adjacent a patient's native aortic valve annulus. The leaflets are typically supported by the annulus inflow portion. The stent typically further includes an aortic outflow portion configured for disposition in the patient's native aorta downstream from at least a portion of the patient's native valsalva sinus (also sometimes called the sinus of valsalva). The stent typically still further includes a plurality of connecting struts that constitute substantially the sole connection between the annulus inflow portion and the aortic outflow portion. The annulus inflow portion typically defines a plurality of commissure tips that are spaced from one another in the annular direction around the annulus inflow portion. The commissure tips are the features of the annulus inflow portion that are closest to the aortic outflow portion. Each of the above-mentioned connecting struts is connected to the annulus inflow portion only at points that are farther from the aortic outflow portion than the commissure tips. In addition, each of the connecting struts is adjacent to an associated one of the commissure tips, and at least one of the struts is positioned for disposition adjacent each side of each of the patient's native aortic valve commissure tips. Each of the connecting struts is constructed to bulge radially outwardly like (and into) the valsalva sinus when the valve is in use in a patient.

Further features of the invention, its nature and various advantages, will be more apparent from the accompanying drawings and the following detailed description.

BRIEF DESCRIPTION OF THE DRAWINGS

FIG. 4 is a view similar to FIG. 2 for another illustrative embodiment in accordance with the invention.

FIG. 5 is a view similar to FIG. 2 for yet another illustrative embodiment in accordance with the invention.

FIG. 7a shows the leaflets of the valve open but greatly simplified. FIG. 7a also shows other possible components added.

FIG. 10 shows the depicted component after it has been cut along an axis that is vertical in FIG. 10 and then laid out flat in the plane in which FIG. 10 is drawn.

DETAILED DESCRIPTION

Many of the principles employed in the prosthetic valves that are shown and described in the above-mentioned reference can be employed in valves in accordance with this invention. Accordingly, the descriptions of some features herein can be somewhat abbreviated because more complete information is already available from the above-mentioned reference. To facilitate comparison, the reference numbers that are used herein for components that are at least generally similar to components in the above-mentioned reference are often (although perhaps not always) related by integer multiples of 1000 to the reference numbers used for those generally similar components in the above-mentioned reference. Thus, for example, component 5010 herein is generally similar to any of components 10, 1010, 2010, 3010, 4010, 5010, etc., in the above-mentioned reference.

Figure 1:
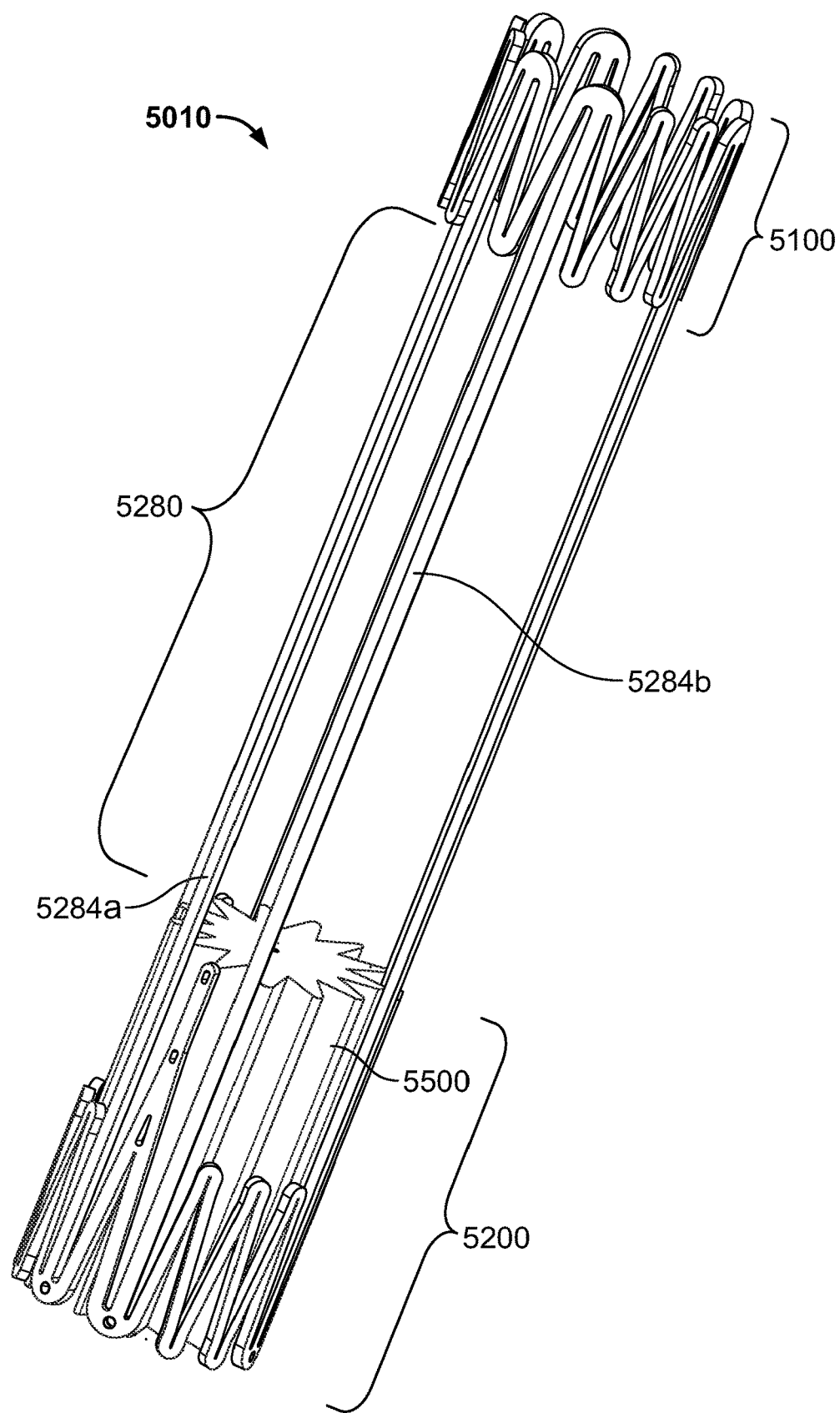
FIG. 1 is a simplified perspective or isometric view of an illustrative embodiment of some components of a prosthetic heart valve in accordance with the invention, in a first possible operating condition of those components.
Figure 2:
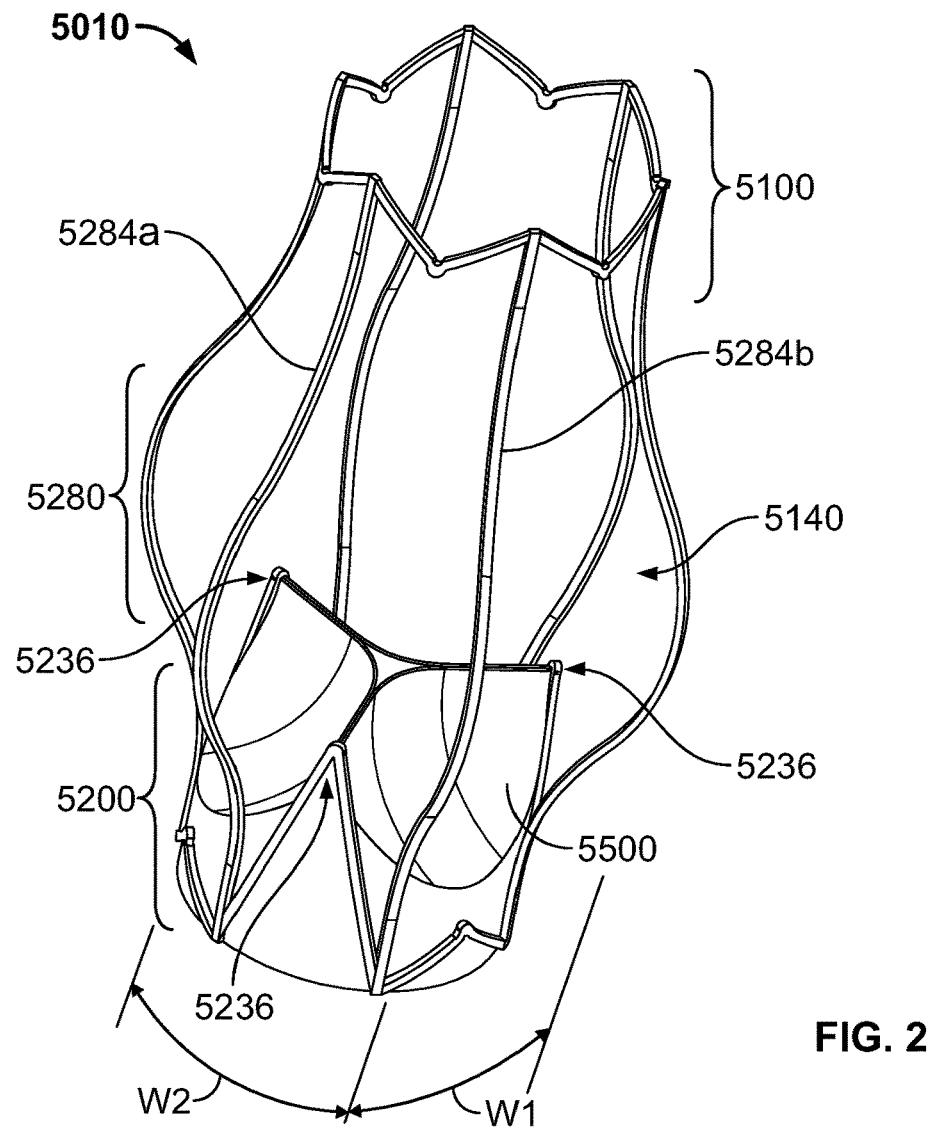
FIG. 2 is a simplified perspective or isometric view of a structure like that shown in FIG. 1, in another possible operating condition of that structure.

FIG. 1 shows some components of an illustrative prosthetic heart valve in accordance with the invention in an annularly or circumferentially collapsed condition for delivery into a patient via relatively small-diameter delivery apparatus. (FIG. 1 has been simplified as explained in more detail in the next paragraph.) Such small-diameter delivery can be used to avoid full open-chest/open-heart surgery. FIG. 2 shows a valve generally like the valve shown in FIG. 1 (although with some differences from what is shown in FIG. 1) after annular or circumferential re-expansion (e.g., via the use of highly-elastic, self-expansion). FIG. 2 thus shows a valve in its deployed condition (i.e., the condition it has when implanted in a patient).

All of the many embodiments shown and described in this specification are annularly or circumferentially collapsible to a delivery condition like that generally illustrated by FIG. 1, and then annularly or circumferentially re-expandable to an implanted or deployed condition like that generally illustrated by FIG. 2.

The valves shown in FIGS. 1 and 2 are intended for implanting within a patient's native aortic valve to mitigate impaired functioning of the native valve. FIGS. 1 and 2 do not necessarily show all features or components of complete valves. For example, some layers of material (e.g., fabric and/or tissue) that may be used around the outside of certain portions of these valves are not shown in FIGS. 1 and 2 to better reveal possible constructional features of other components of the valves. In particular, FIGS. 1 and 2 primarily show the collapsible/expandable, metal, stent frame 5010 of the depicted valves, and the flexible leaflets 5500 of these valves. (Again, fabric material (not shown) can be used outside or inside stent frame 5010 at the inflow section of the stent.) Examples of suitable materials for leaflets 5500 include biological tissue, polymer, thin metal, reinforced polymer, etc. As used herein, the term "biological tissue" includes such things as actual harvested porcine valves, bovine pericardium, and the like.

As in the above-mentioned reference, stent 5010 includes an aortic outflow portion 5100 and an annulus inflow portion 5200. Portions 5100 and 5200 are connected to one another substantially solely by at least one connecting strut 5284. All of these structures (5100, 5200, and 5284) are annularly or circumferentially collapsible (FIG. 1) and re-expandable (FIG. 2). This includes leaflets 5500. When the valve is in place in a patient's native aortic valve, the prosthetic valve is re-expanded as shown in FIG. 2. When the valve is thus re-expanded at the implant site in the patient, annulus inflow portion 5200 is typically adjacent the patient's native aortic valve annulus, aortic outflow portion 5100 is in the aorta downstream from the valsalva sinus (or downstream from at least part of the valsalva sinus), and connecting struts 5284 pass through the valsalva sinus (or through at least part of the valsalva sinus). In addition, respective connecting struts 5284 preferably pass near and on each side of each of the patient's native valve commissures. This last point will be described in greater detail later in this specification. Because portion 5100 thus resides in the patient's aorta when the valve is implanted, portion 5100 is generally referred to herein as the aortic outflow portion.

Annulus inflow portion 5200 includes three commissure posts or tip regions 5236 that are equally spaced from one another around the valve. In the FIG. 2 embodiment, for example, each of the commissure tips 5236 is at the free apex of a V-shaped commissure post structure that extends down from the tip as viewed in FIG. 2. Each of these V-shaped commissure post structures is cantilevered from at least an associated pair of annularly spaced points on remaining structure of annulus inflow portion 5200. Cantilevering the commissure posts in this way facilitates giving the commissure posts desirable flexibility, which includes flexibility in a direction that is radial of the valve at the location of the tip or free end of each commissure post.

Adjacent each of commissure tips 5236, there is an associated pair of connecting struts 5284*a* and 5284*b*. One of these struts 5284*a* is on one side of the associated commissure tip 5236 in a circumferential direction around the valve, and the other strut 5284*b* is on the other side of the associated commissure tip in a circumferential direction around the valve. Each of these struts 5284 connects to the annulus inflow portion 5200 at a point that is well below the associated commissure tip 5236. As in the above-mentioned reference, this makes it possible for the commissure post structure below each tip 5236 to be desirably flexible relatively independently of struts 5284. It also facilitates giving commissure post structures 5236 and struts 5284 shapes in the radial direction (i.e., inwardly and outwardly of the valve as a whole) that can be relatively independent of one another. For example, commissure post structures 5236 can go relatively straight up from the base of annulus inflow portion 5200, while struts 5284 can bulge radially out from the geometric cylindrical surface in which the commissure post structures lie. (The entire population of connecting struts 5284 in a valve may sometimes be referred to collectively by reference number 5280.)

The connecting struts 5284*a* and 5284*b* that are adjacent to each commissure tip 5236 can remain relatively close to one another and to that commissure tip as they extend to aortic outflow portion 5100. Thus, for example, in the annular (circumferential) direction around the expanded valve (e.g., as in FIG. 2), and at the level (in the axial direction along the valve) of commissure tips 5236, the struts 5284*a* and 5284*b* that are associated with each commissure tip 5236 tend to be closer to one another than they are to the circumferentially nearest strut 5284 that is associated with another commissure tip. This helps to give the valve relatively large openings 5140 between the struts 5284 that are associated with annularly adjacent ones of the commissure tips. This may be desirable to help the valve avoid occluding the coronary ostia of the patient's coronary arteries. These ostia are located in the valsalva sinus approximately midway between axial projections of certain of the native aortic valve commissures (see FIG. 3, which is discussed in more detail later in this specification).

To quantify an aspect of what is said above, at the level of commissure tips 5236 in the circumferentially expanded valve shown in FIG. 2, the width W1 of the opening 5140 between the struts 5284 associated with two annularly (or circumferentially) adjacent commissures is preferably greater than the width W2 between the struts associated with a given commissure. More preferably W2 is less than about one-half of W1.

Figure 3:
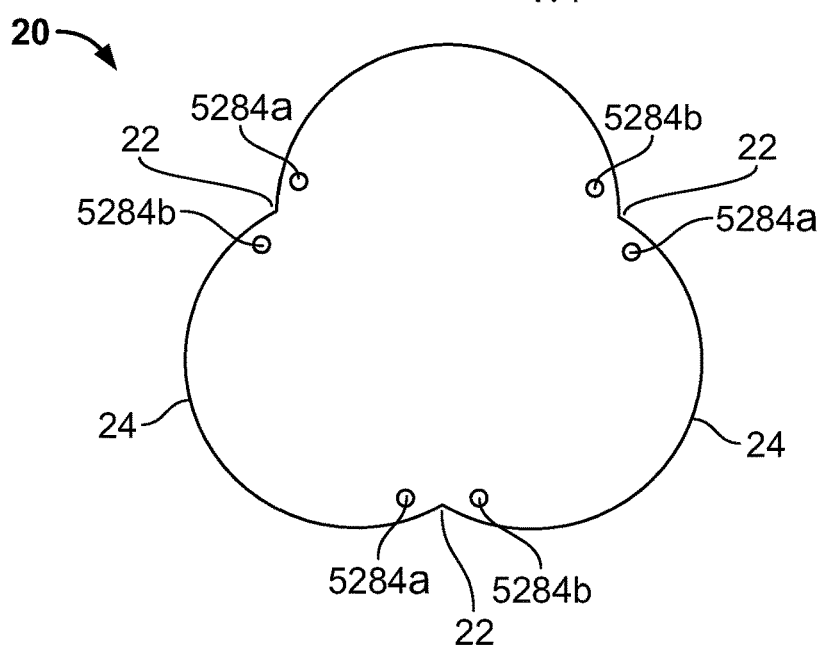
FIG. 3 is a simplified cross-sectional view of a patient's native tissue, with some components of an implanted valve of this invention visible in that native tissue structure.

FIG. 3 shows the approximate cross-sectional shape of a typical native valsalva sinus 20. Axial projections of the commissures of the native aortic valve are indicated at 22. Locations of coronary artery ostia are indicated at 24. Between each annularly adjacent pair of commissure projections 22, valsalva sinus 20 has an outwardly bulging lobe. The two connecting struts 5284a and 5284b associated with each prosthetic valve commissure pass axially through the valsalva sinus on respective opposite sides of the commissure projection 22 that is associated with the prosthetic valve commissure 5236 that is aligned with that projection 22. These struts 5284a and 5284b also bulge radially out to follow the bulge of the adjacent valsalva sinus tissue (see again FIG. 2). From this it will be appreciated that the shape and locations of struts 5284a and 5284b can help to anchor the prosthetic valve in the desired axial and angular location in the patient. The presence of a pair of struts 5284a and 5284b adjacent to each side of each commissure projection 22 can help prevent the prosthetic valve from rotating in the patient about the longitudinal axis of the valve. In addition, the outward bulging of struts 5284 into the outward bulging of the valsalva sinus lobes can help prevent the prosthetic valve from moving in either direction along the longitudinal axis of the valve. These anchoring aspects of connecting struts 5284 passing through valsalva sinus 20 can be in addition to other anchoring aspects that the prosthetic valve may have (e.g., as shown and described in the above-mentioned reference).

When deployed in a patient, all of the various prosthetic valve embodiments that are shown and described in this specification have outwardly bulging connecting struts 5284 like those shown in FIG. 2, with spacing (e.g., W1 and W2) like that shown in FIG. 2, and with positioning of the struts relative to native valve commissure projections 22 like that shown in FIG. 3.

FIG. 4 shows an alternative embodiment of stent frame 5010 (now labelled 5010a in FIG. 4). Although there are some differences between stent 5010a and stent 5010, the same reference numbers are generally used for generally similar parts of both embodiments (i.e., the embodiment of FIG. 4 and the earlier-described embodiment of FIGS. 1 and 2). Whereas in the embodiment of FIGS. 1 and 2 both of aortic outflow portion 5100 and annulus inflow portion 5200 are annularly continuous all the way around stent 5010, in the FIG. 4 embodiment stent 5010a is annularly continuous as a whole, but each of portions 5100 and 5200 has several interruptions in the annular (circumferential) direction. In particular, where portion 5100 extends between two annularly adjacent connecting struts 5284, portion 5200 does not extend between those two struts; and where portion 5200 extends between two annularly adjacent struts 5284, portion 5100 does not extend between those two struts. In other respects the prosthetic heart valve shown in FIG. 4 can be similar to what is shown in FIGS. 1 and 2, and it can implant in a patient similarly to what is shown in FIG. 3.

An embodiment like that shown in FIG. 4 may fit better in certain patients. For example, it may fit better in an irregular native aortic valve annulus (e.g., an annulus that is made irregular by a congenital defect or by the presence of calcified native leaflet material). A purpose for this embodiment is to provide flexibility in sizing of the distal section (e.g., aortic outflow portion 5100). The intention of the inflow side is not to conform to native geometry, but rather to remodel that geometry to allow the prosthetic valve to function optimally. The presence of hard calcification can impact the final deployed shape. This design allows some balance between remodeling and conforming.

FIG. 5 shows another alternative embodiment of stent frame 5010 (now referenced 5010b in FIG. 5). Again, the same reference numbers used earlier are used again for generally similar elements of FIG. 5. In FIG. 5 aortic outflow portion 5100 is annularly continuous (as in FIGS. 1 and 2), but annulus inflow portion 5200 is annularly interrupted in the same way that the annulus inflow portion is interrupted in FIG. 4. In other respects the FIG. 5 embodiment may be similar to the previously described embodiments, and it can be implanted in a patient as illustrated in part in FIG. 3. Like the embodiment of FIG. 4, the embodiment of FIG. 5 may fit better in certain patients, such as patients with an irregular native aortic valve annulus.

Note that in any of the embodiments shown and described herein, the stent frame can be provided with eyelets, apertures, or other features that facilitate attachment of the leaflets and other materials to the stent. Examples will be shown and described later in this specification.

Figure 6:
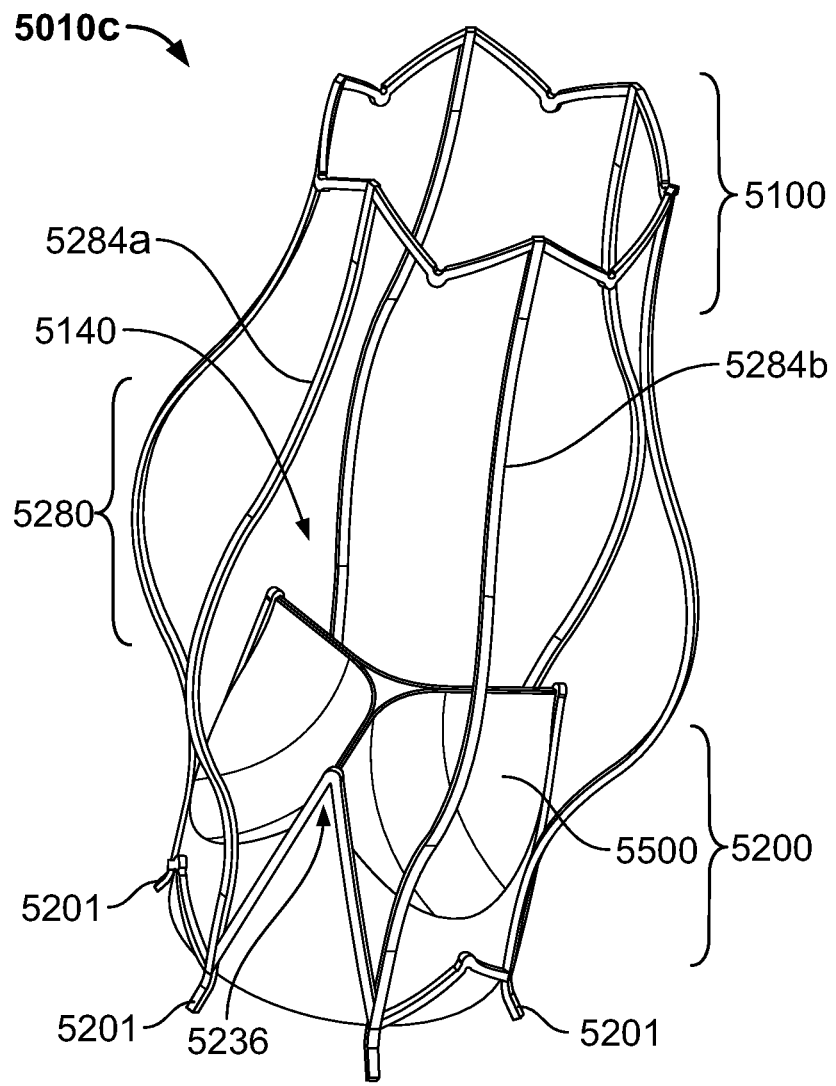
FIG. 6 is a view similar to FIG. 2 for still another illustrative embodiment in accordance with the invention.

FIG. 6 shows yet another alternative embodiment of stent frame 5010 (now numbered 5010c in FIG. 6). Once again, the same reference numbers used earlier are used again for generally similar elements in FIG. 6. Stent 5010c is basically the same as stent 5010, with the addition of a plurality of anchor members 5201 that are resiliently biased to incline outwardly from annulus inflow portion 5200. During delivery of the valve into a patient in an annularly compressed or collapsed condition, anchor members 5201 can be deflected substantially parallel to the longitudinal axis of the valve. When the valve is released from such annular compression for deployment in the patient (e.g., by pushing the valve out of the distal end of a delivery tube that keeps the valve annularly compressed), anchor members 5201 spring out as shown in FIG. 6. In this condition anchor members 5201 engage (e.g., penetrate) the adjacent native tissue of the patient and thereby help to hold the valve in place in the patient. (FIG. 3 again applies to the deployed condition of the FIG. 6 embodiment.)

It will be appreciated that anchors like 5201 can be used at any of many different locations on the stent frame 5010, etc., of any of the embodiments shown herein. As just one example of other possible locations for anchors like 5201, such anchors could be alternatively or additionally located on the upper (outflow) edge of any of the stent frame shown herein.

Figure 7A:
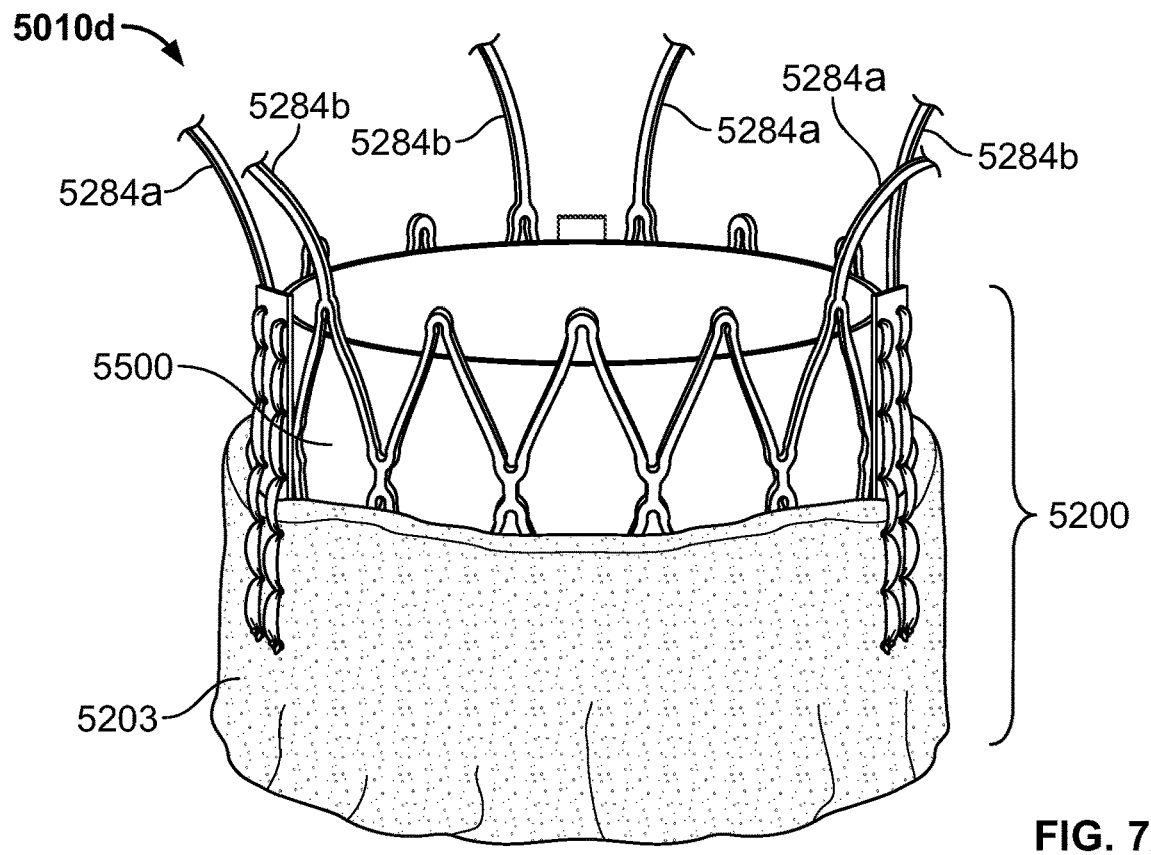
FIG. 7a is a view similar to part of FIG. 2 for yet another illustrative embodiment in accordance with the invention.
Figure 7B:
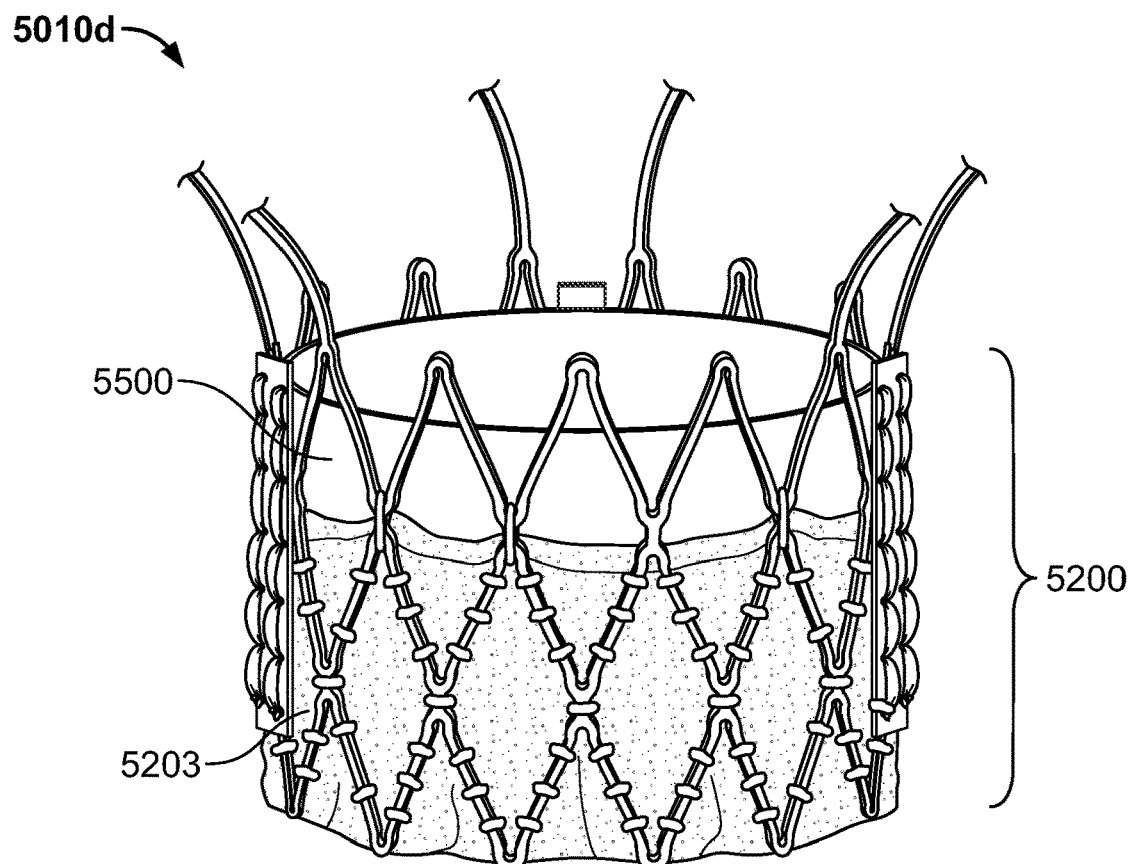
FIG. 7b is a view similar to FIG. 7a for another illustrative embodiment in accordance with the invention.

FIGS. 7a and 7b show illustrative embodiments in which an inflow-end cuff 5203 (e.g., of fabric) is included. Except for the addition of inflow cuff 5203, the embodiments shown in FIGS. 7a and 7b can be similar to any of the other embodiments shown herein. (FIGS. 7a and 7b include greatly simplified depictions of the leaflet structure 5500 in the open condition.) Inflow cuff 5203 preferably extends annularly all the way around the valve adjacent to its inflow edge. (As always throughout this specification, "inflow" refers to the direction of blood flow through the valve after it has been implanted and is in use in a patient.) The cuff fabric material can be attached to the outside (FIG. 7a), the inside (e.g., between stent frame 5010d and leaflets 5500 as shown in FIG. 7b), or directly below the stent frame in another embodiment. Inside and outside are preferred because this allows for better integration of the leaflet material 5500 onto the stent 5010d, because the leaflet materials utilize the presence of the cuff fabric material during assembly and integration. This also provides a more durable design. When the valve is in the expanded state, the cuff fabric material should lie flat on the inside or outside of the stent frame 5010d. The presence of the fabric 5203 helps promote tissue in-growth after the valve has been implanted. This helps to seal the valve against perivalvular leakage. (FIG. 3 again applies to the deployed condition of the FIGS. 7a and 7b embodiments.)

Figure 8:
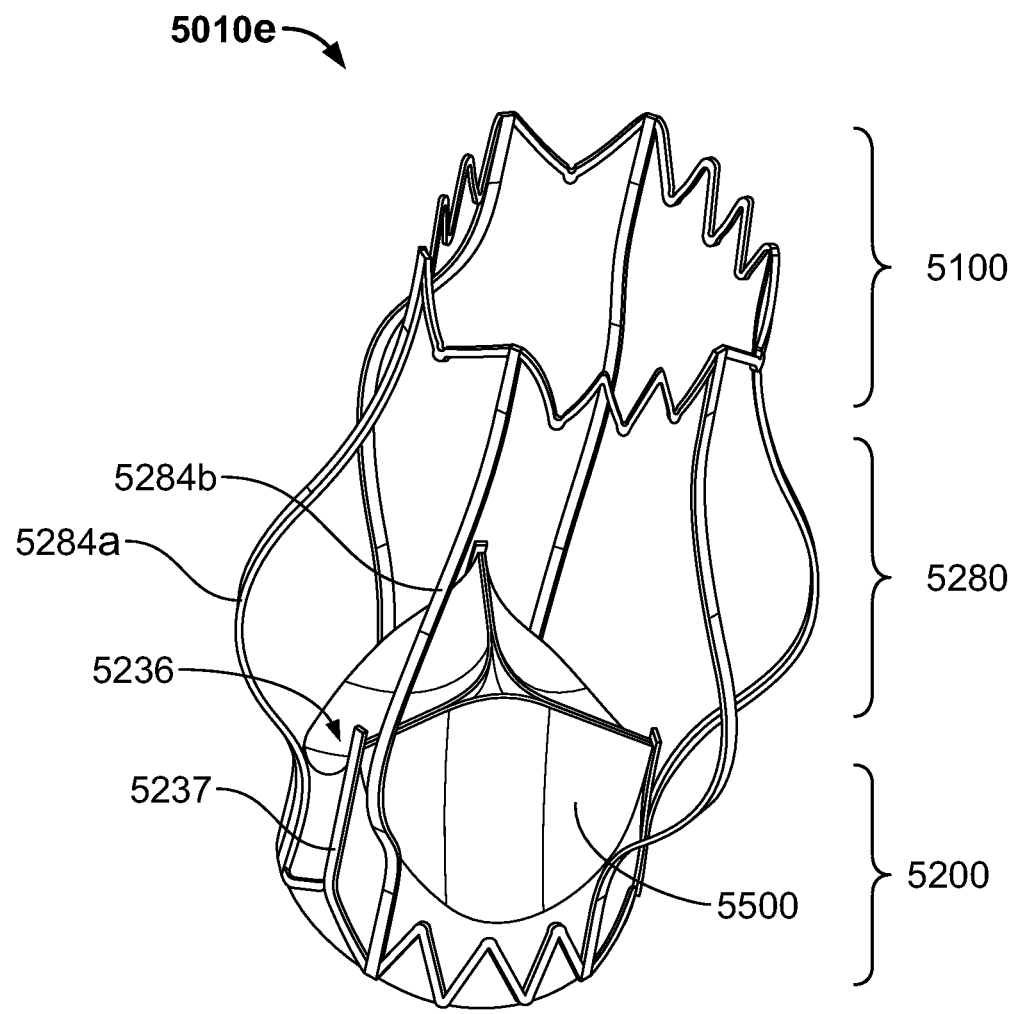
FIG. 8 is a view similar to FIG. 2 for still another illustrative embodiment in accordance with the invention.
Figure 9:
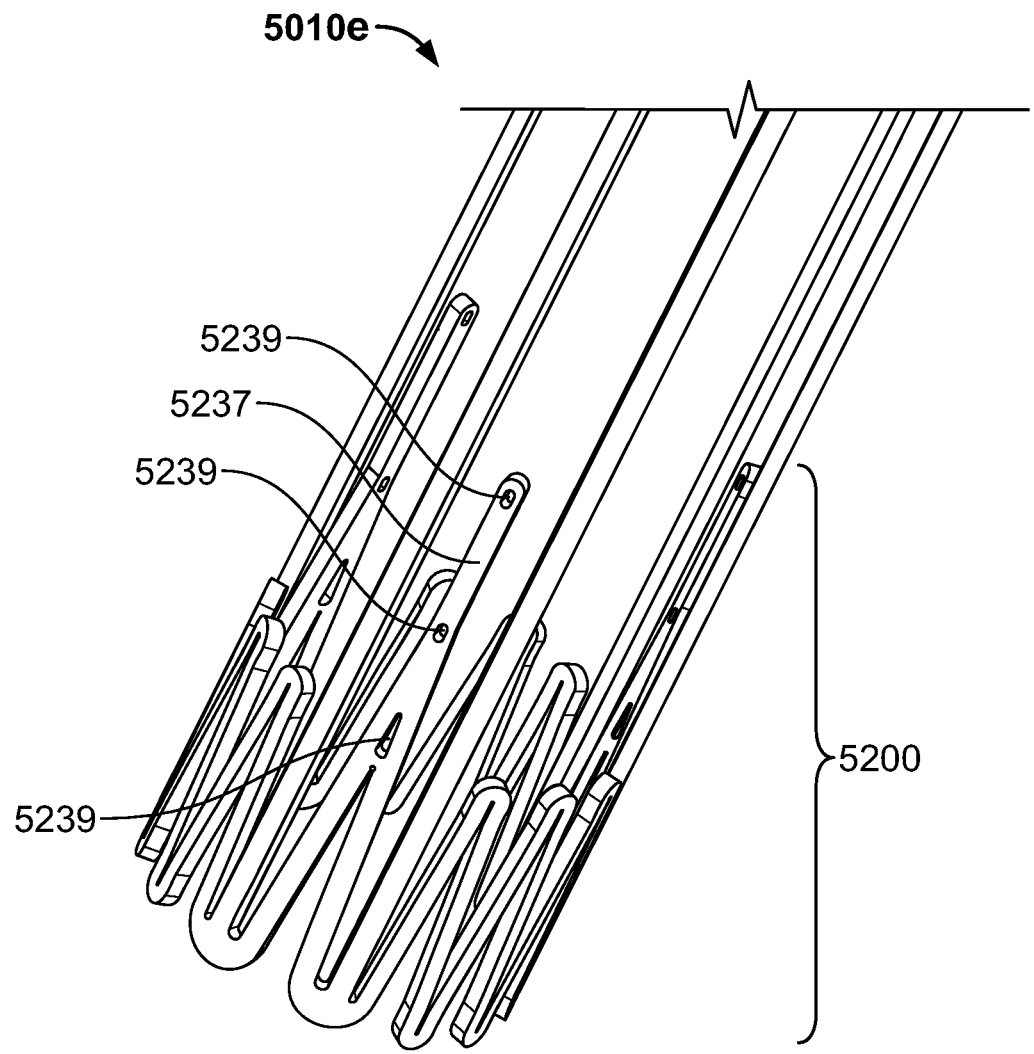
FIG. 9 shows a portion of the FIG. 8 embodiment in another operating condition of the apparatus.

FIGS. 8 and 9 show another illustrative embodiment in which stent frame 5010e includes commissure regions that are somewhat more post-like, as at reference number 5237. (FIG. 8 shows the apparatus in its annularly expanded, deployed condition. FIG. 9 shows part of the same apparatus in its annularly collapsed, delivery condition.) Making each prosthetic valve commissure region more like a single upstanding post 5237 may enhance each such commissure region's independent flexibility (i.e., its ability to flex independently of other parts of supporting structure 5010e). Amplifying the description of this aspect of FIGS. 8 and 9 somewhat, in embodiments of this type, each commissure tip 5236 of the valve is at the free end of a respective single structural member 5237 that is cantilevered from a respective single point on remaining structure of annulus inflow portion 5200.

FIGS. 8 and 9 also show examples of how stent frame 5010e may be provided with apertures 5239 for facilitating attachment of other components (e.g., leaflets 550) to the stent frame. Another possible use for apertures like 5239 is for helping to releasably secure a prosthetic valve in accordance with the invention to delivery system apparatus for the valve. For example, wires or suture material may pass through apertures like 5239 from and/or to delivery apparatus to help releasably hold the valve in the delivery apparatus until the valve is ready to be deployed into the patient. FIG. 3 again applies to deployment of the FIG. 8-9 embodiment.

Figure 10:
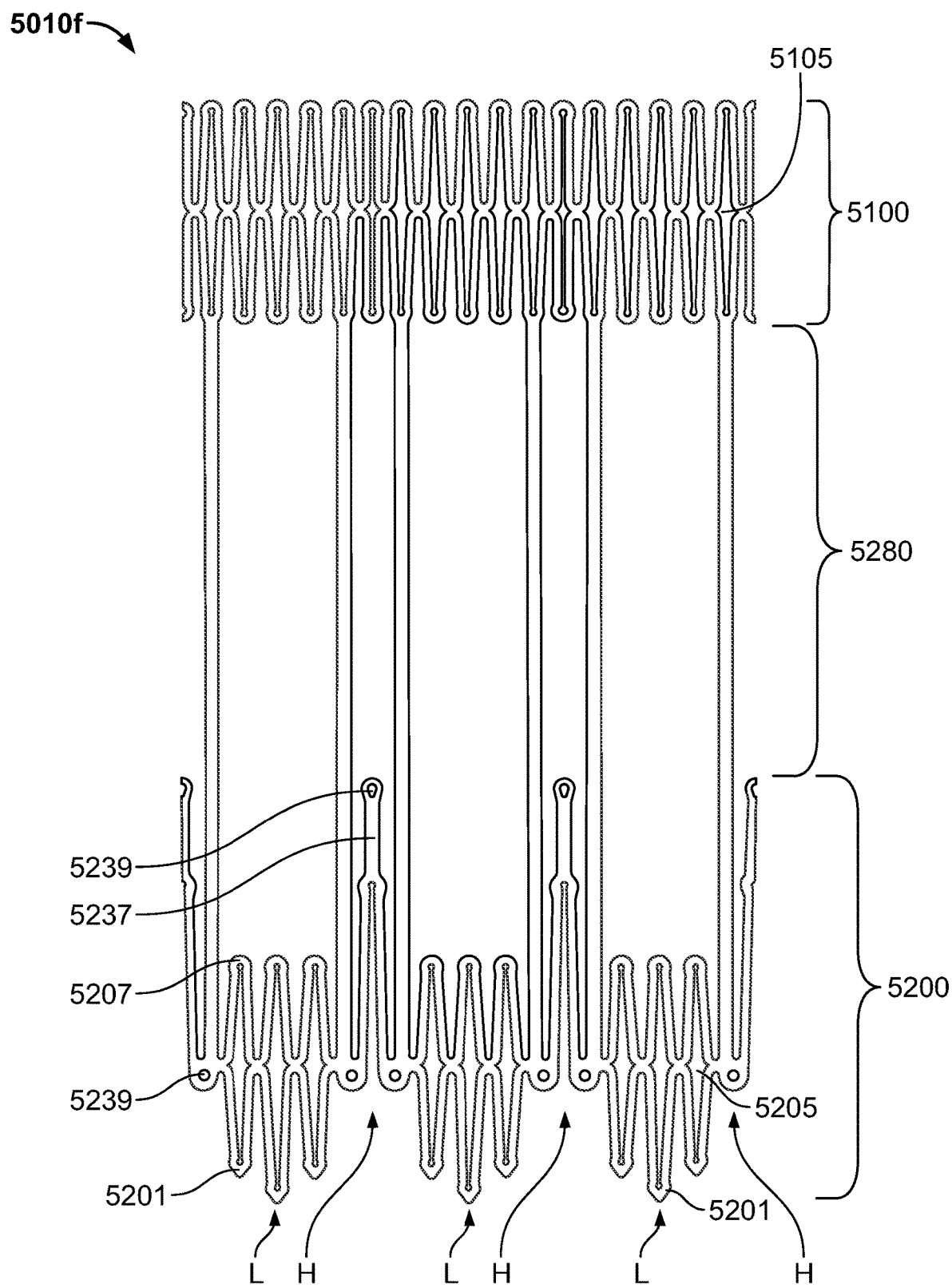
FIG. 10 is a simplified elevational view of a portion of yet another illustrative embodiment in accordance with the invention.

FIG. 10 shows an example of a stent frame 5010f that (solely for purposes of illustration herein) has been cut along a longitudinal axis and then flattened. In the FIG. 10 embodiment the inflow edge of the stent frame (toward the bottom of FIG. 10) is scalloped or recessed so that it is relatively "high" in the vicinity of each commissure region 5236 and relatively "low" between each annularly adjacent pair of commissure regions. The high areas are pointed out by reference characters H, and the low areas are pointed out by reference characters L. Making the inflow edge of stent frame 5010f relatively high adjacent the aortic valve commissures helps the prosthetic aortic valve avoid possibly impinging on the patient's native mitral valve, and may also have other advantages.

FIG. 10 also illustrates some other possible variations. For example, FIG. 10 shows another possible arrangement of apertures 5239 like those mentioned above. FIG. 10 shows another arrangement of the circumferentially collapsible/expandable ring structures that can be used in areas 5100 and 5200. In this example these ring structures include four-sided, open-centered cells (e.g., 5105 and 5205) that can expand in the left-right direction as viewed in FIG. 10 to annularly expand the stent frame for deployment in the patient, or that can shrink in the left-right direction as viewed in FIG. 10 to annularly collapse the stent frame for delivery into the patient. FIG. 10 shows these cells 5105 and 5205 in their annularly collapsed condition. A row of such cells can be thought of as two side-by-side serpentine or undulating rings that are 180° out of phase with one another and that have been joined together at adjacent peaks in their undulations. FIG. 10 also shows another example of use of barbs 5201 like those described earlier in this specification.

Figure 11:
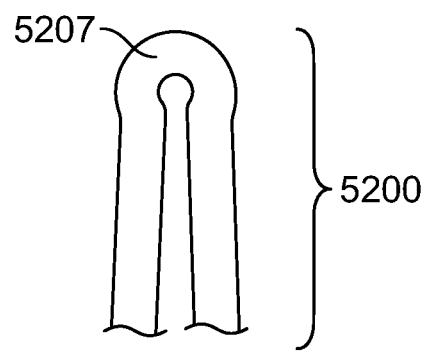
FIG. 11 is an enlargement of a representative portion of what is shown in FIG. 10.
Figure 12:
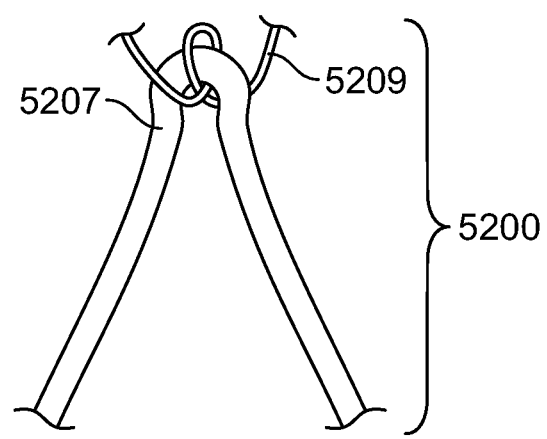
FIG. 12 shows the FIG. 11 structure in another operating condition.

FIGS. 11 and 12 show a representative detail from FIG. 10. It will be understood that this type of feature can be used at any suitable location(s) in any of the embodiments shown herein. The feature detailed in FIGS. 11 and 12 is a rounded corner 5207 between otherwise relatively straight members of cells like 5205 or other similar serpentine or undulating ring structures. (Again, this feature can also be used elsewhere such as in region 5100.) FIG. 11 shows one representative rounded corner 5207 in an annularly collapsed structure. Note that in FIG. 11 rounded corner 5207 preferably has an overall C shape. FIG. 12 shows the same rounded corner after annular expansion of the structure. Now (i.e., in FIG. 12) corner 5207 has opened up somewhat to have a more nearly U shape. Use of these rounded corners helps to avoid stress concentration where the members of the cellular or serpentine structure change direction. This can improve the performance and extend the life of the structure. Also, upon expansion, these rounded corners tend to open up slightly (e.g., from a C shape to a U shape). This can facilitate leaflet attachment by providing locations through which suture material 5209 can be passed (e.g., as shown in FIG. 12).

Figure 13:
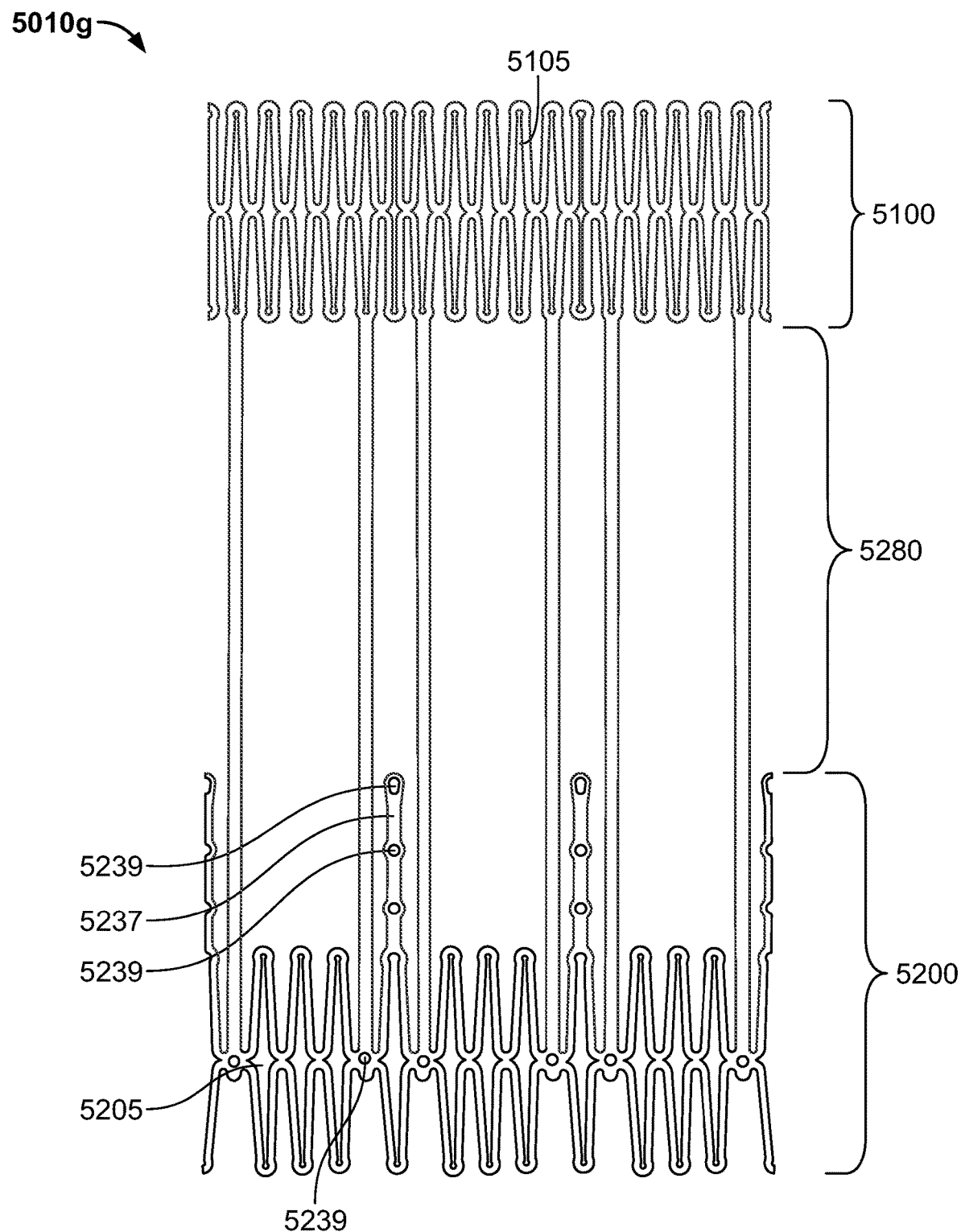
FIG. 13 is a view similar to FIG. 10 for another illustrative embodiment in accordance with the invention.

FIG. 13 shows (using the same general type of depiction as in FIG. 10) yet another alternative embodiment in which aortic outflow portion 5100 has more closed cells 5105 than annulus inflow portion 5200. This may facilitate annular expansion of aortic outflow portion 5100 to a larger diameter than annulus inflow portion 5200. FIG. 13 also shows another example of how and where aperture 5239 may be provided in stent frame 5010g to facilitate attachment of leaflets and other materials to the stent frame. (FIG. 3 again applies to deployment of embodiments like those shown in FIGS. 10 and 13.)

Figure 14:
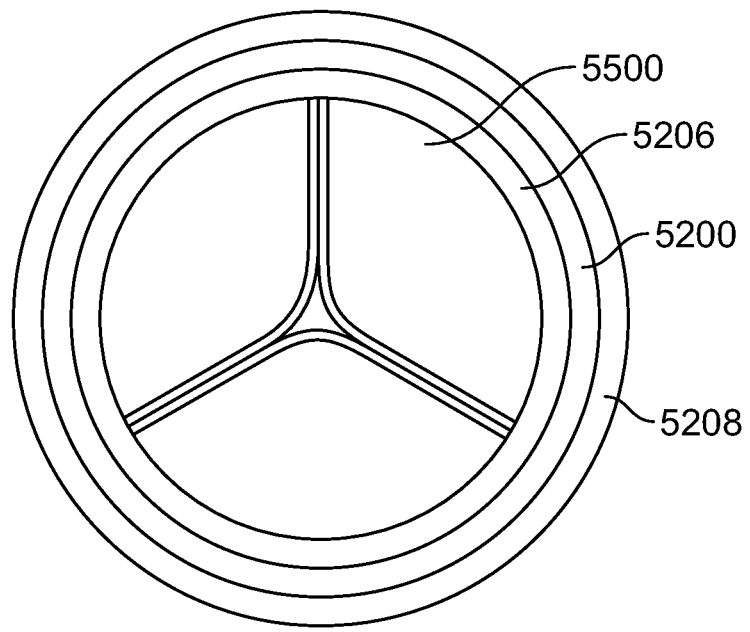
FIG. 14 is a simplified view looking down on the inflow portion of an illustrative embodiment of a prosthetic heart valve in accordance with the invention.

FIG. 14 shows that a valve in accordance with the invention may have fabric 5206 mounted internally of any portion of stent frame 5010 (the FIG. 14 example shows fabric 5206 between annulus inflow portion 5200 and leaflets 5500). FIG. 14 also shows that a valve in accordance with the invention may have fabric 5208 mounted externally of any portion of stent frame 5010 (again, the FIG. 14 example shows fabric 5208 around the outside of annulus inflow portion 5200). Although FIG. 14 shows fabric around both the inside and outside of a portion of stent frame 5010, it will be understood that fabric may be used in only one of these locations if desired. Some or all of the fabric like 5206 and/or 5208 may form the cuff 5203 shown in FIG. 7a or 7b.

Figure 15:
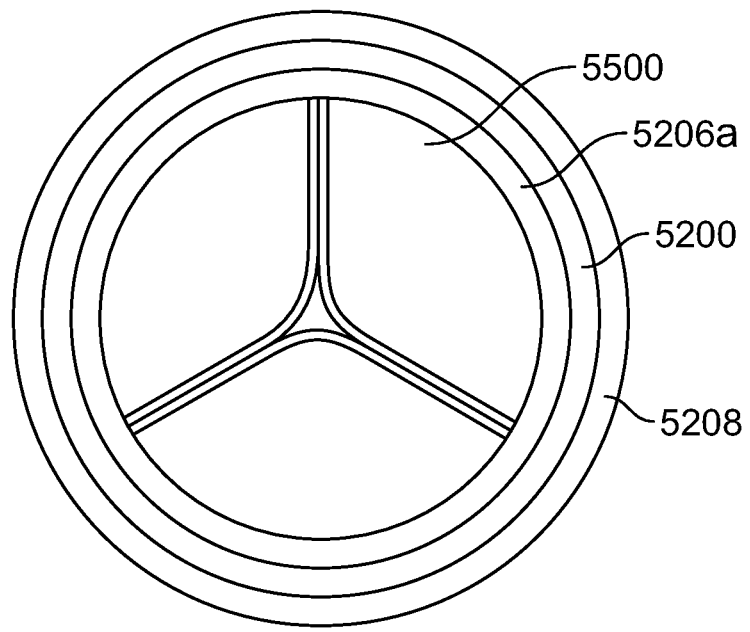
FIG. 15 is a simplified view looking down on the inflow portion of another illustrative embodiment of a prosthetic heart valve in accordance with the invention.

FIG. 15 shows that a valve in accordance with the invention may have tissue material 5206a as a buffer between the stent frame 5010 and coating leaflets 5500 to prevent abrasion of the leaflets by the stent frame and provide longer durability performance for the valve. In the example shown in FIG. 15, tissue material 5206a is between annulus inflow portion 5200 and leaflets 5500. Tissue material 5206a is preferably thinner than the material used for leaflets 5500.

Figure 16:
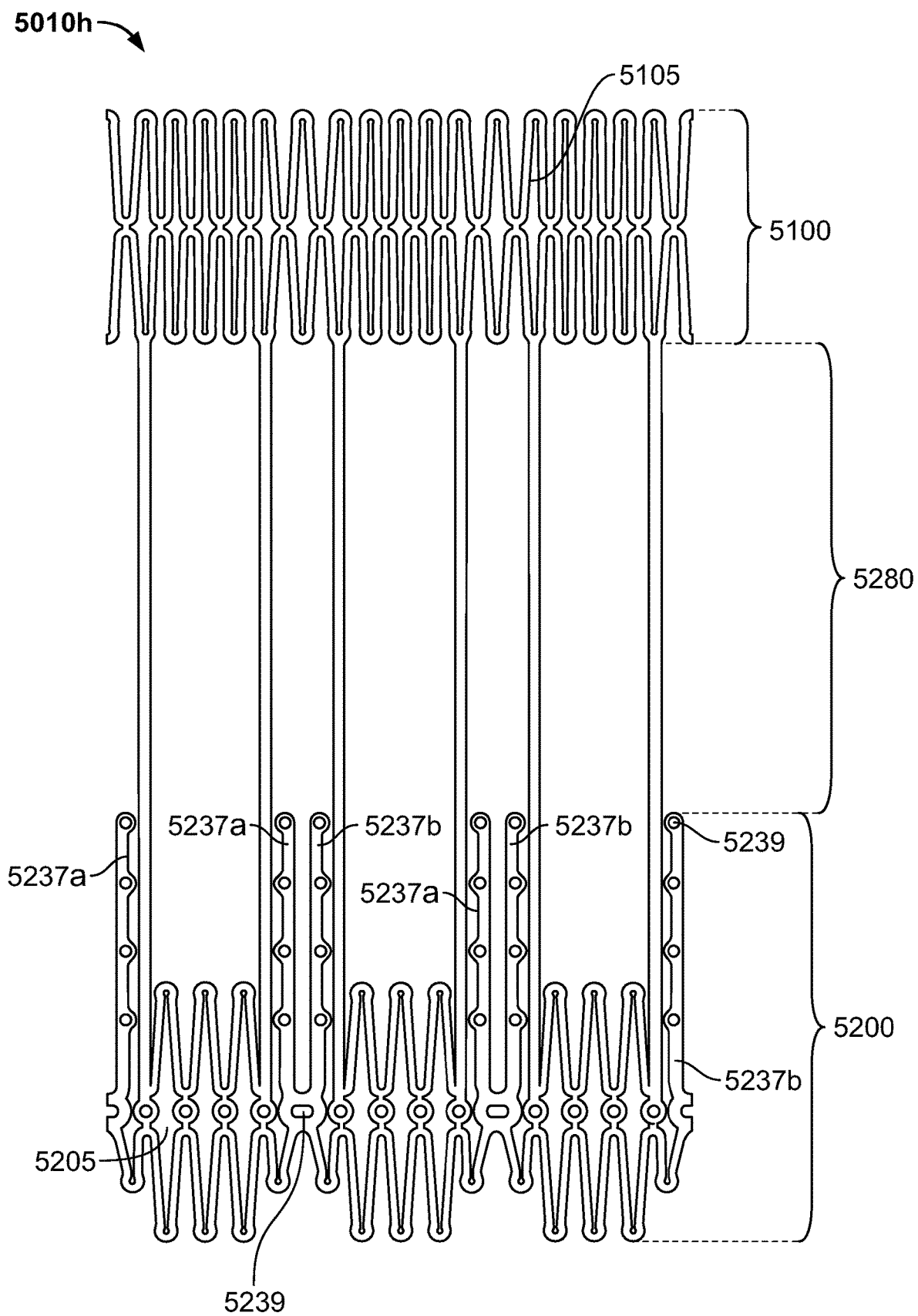
FIG. 16 is a view similar to FIG. 13 for another illustrative embodiment in accordance with the invention.

FIG. 16 shows (using the same general type of depiction as in FIG. 13) another illustrative embodiment of stent frame 5010h in which each commissure post region 5237 is bifurcated into two, substantially parallel, independently cantilevered post members 5237a and 5237b.

In general, it is preferred that the circumferential (annular, radial) collapse and re-expansion of prosthetic valves in accordance with this invention is elastic or at least mostly elastic. However, part or all of such collapse and/or re-expansion may alternatively or additionally result from use of shape-memory properties of the material of the stent frame (e.g., 5010) of the valve. As still another possibility, some or all of the collapse and/or re-expansion of the valve may be plastic. For example, such plastic re-expansion may be produced by inflation of a balloon (e.g., on a catheter) inside the valve.

It will be understood that the foregoing is only illustrative of the principles of the invention, and that various modifications can be made by those skilled in the art without departing from the scope and spirit of the invention. For example, the number of undulations or cells used in aortic outflow portion 5100 and/or annulus inflow portion 5200 can be different (more or less) than the numbers shown in the FIGS. that form part of this disclosure.

The invention claimed is:

1. A prosthetic heart valve, comprising:
a stent frame having an expanded condition and a collapsed condition, the stent frame including an inflow portion, an outflow portion, and a plurality of connecting struts, each of the connecting struts having a first end connected to the inflow portion and a second end connected to the outflow portion, the inflow portion including a plurality of commissure structures spaced from one another in an annular direction around the inflow portion, each of the commissure structures having a first portion with a first end and a second portion, the commissure structure being connected only to a respective pair of points on a remaining structure of the inflow portion, the second portion of the commissure structure including a post member extending from the first portion toward the outflow portion, the post member having a free end; and
a plurality of valve leaflets supported by the inflow portion.

2. The prosthetic heart valve as claimed in claim 1, wherein each of the connecting struts is connected to the inflow portion only at points that are farther from the outflow portion than the free ends of the post members.

3. The prosthetic heart valve as claimed in claim 1, wherein an edge of the inflow portion that is most remote from the outflow portion includes a recessed edge portion aligned with at least one of the commissure structures, the recessed edge portion being closer to the outflow portion than other portions of the edge of the inflow portion.

4. The prosthetic heart valve as claimed in claim 1, wherein the second portion of each of the commissure structures includes two post members spaced apart from one another in the annular direction.

5. The prosthetic heart valve as claimed in claim 4, wherein each of the post members includes a plurality of apertures.

6. The prosthetic heart valve as claimed in claim 1, wherein the inflow portion includes a plurality of diamond-shaped cells, a group of the diamond-shaped cells being interposed between adjacent ones of the commissure structures.

7. The prosthetic heart valve as claimed in claim 6, wherein each of the diamond-shaped cells has a first end pointing toward the outflow portion and a second end pointing away from the outflow portion, the first end and the second end each having a C shape in the collapsed condition of the stent frame.

8. The prosthetic heart valve as claimed in claim 6, wherein the outflow portion includes a plurality of diamond-shaped cells, the second end of each of the connecting struts being connected to a respective one of the diamond-shaped cells in the outflow portion.

9. The prosthetic heart valve as claimed in claim 8, wherein each of the diamond-shaped cells in the outflow portion has a first end pointing toward the inflow portion and a second end pointing away from the inflow portion, and the second end of each of the connecting struts is connected to the first end of the diamond-shaped cells in the outflow portion.

10. The prosthetic heart valve as claimed in claim 9, wherein the first end of each of the diamond-shaped cells in the outflow portion and the second end of each of the diamond-shaped cells in the outflow portion has a C shape in the collapsed condition of the stent frame.

11. The prosthetic heart valve as claimed in claim 1, wherein the inflow portion includes a single row of struts arranged in a zig-zag pattern, a group of the struts being arranged between adjacent ones of the commissure structures.

12. The prosthetic heart valve as claimed in claim 1, wherein the outflow portion includes a single row of struts arranged in a zig-zag pattern, the second end of each of the connecting struts being connected to a respective one of the struts in the outflow portion.

13. The prosthetic heart valve as claimed in claim 12, wherein the zig-zag pattern includes first pairs of struts forming peaks relatively close to the inflow portion and second pairs of struts forming peaks relatively far away from the inflow portion, and the second end of each of the connecting struts is connected to the peaks relatively far from the inflow portion.

14. The prosthetic heart valve as claimed in claim 1, wherein each of the post members includes a plurality of apertures.

15. The prosthetic heart valve as claimed in claim 1, further comprising fabric outside at least a portion of the stent frame.

16. The prosthetic heart valve as claimed in claim 1, wherein each of the commissure structures has an associated pair of the connecting struts, the connecting struts in the pair being disposed on opposite sides of the commissure structure in the annular direction.

17. The prosthetic heart valve as claimed in claim 1, further comprising a plurality of anchor members that are resiliently biased to incline outwardly from the stent frame in the expanded condition, the anchor members being connected to the stent frame only at positions that are not between the inflow portion and the outflow portion.

* * * * *